United States Patent
Kaestle et al.

[11] Patent Number: 5,776,059
[45] Date of Patent: Jul. 7, 1998

[54] SENSOR FOR PERFORMING MEDICAL MEASUREMENTS, PARTICULARLY PULSOXIMETRY MEASUREMENTS ON THE HUMAN FINGER

[75] Inventors: Siegfried Kaestle, Nufringen; Martin Guenther, Wildberg-Sulz, both of Germany

[73] Assignee: Hewlett-Packard Company, Palo Alto, Calif.

[21] Appl. No.: 731,169

[22] Filed: Oct. 10, 1996

[30] Foreign Application Priority Data

Nov. 8, 1995 [DE] Germany .................. 195 41 605.8

[51] Int. Cl.$^6$ ........................................ A61B 5/00
[52] U.S. Cl. ........................................ 600/340; 600/344
[58] Field of Search ................................ 128/633, 664, 128/665, 666, 667; 600/322, 323, 324, 326, 340, 344, 473, 476, 479

[56] References Cited

U.S. PATENT DOCUMENTS

| | | |
|---|---|---|
| 4,685,464 | 8/1987 | Goldberger et al. . |
| 4,825,872 | 5/1989 | Tan et al. ............... 128/633 |
| 4,867,165 | 9/1989 | Noller et al. ............ 128/633 |
| 5,035,243 | 7/1991 | Muz . |
| 5,125,403 | 6/1992 | Culp ..................... 128/633 |
| 5,337,744 | 8/1994 | Branigan ................ 128/633 |
| 5,392,777 | 2/1995 | Swedlow et al. . |

FOREIGN PATENT DOCUMENTS

| | | |
|---|---|---|
| 0262779A1 | 4/1988 | European Pat. Off. . |
| 0 481 612 A1 | 4/1992 | European Pat. Off. . |
| 0481612A1 | 4/1992 | European Pat. Off. . |
| 0572684A1 | 12/1993 | European Pat. Off. . |
| 3703458C2 | 8/1988 | Germany . |
| 06327657 A | 11/1994 | Japan . |

OTHER PUBLICATIONS

Medizintechnik, 1991, H. Schubert, pp. 74-76, "Meβtechnik in der medizinischen Diagnostik".

Primary Examiner—Jennifer Bahr
Assistant Examiner—Eric F. Winaker

[57] ABSTRACT

A sensor performs medical measurements, particularly pulsoximetric measurements, and is attached or otherwise adhered to a human fingernail or toenail by an inwardly concave, first casing part of a sensor. Electromagnetic, particularly optical, transmitting elements and receiving elements permit the measurement of the radiation reflected by or transmitted through the tissue. The sensor is easy to apply, allows a long application period and is reusable.

15 Claims, 3 Drawing Sheets

SENSOR FOR PERFORMING MEDICAL MEASUREMENTS, PARTICULARLY PULSOXIMETRY MEASUREMENTS ON THE HUMAN FINGER

DESCRIPTION

1. Field of the Invention

The present invention relates to a sensor for performing medical measurements, in which electromagnetic waves are irradiated into the human tissue and the characteristics of the transmitted or reflected radiation are measured. In detail, the invention more particularly deals with a sensor suitable for performing pulsoximetric measurements.

2. Background of the Invention

The problem of the invention is described hereinafter using the example of pulsoximetry. However, it is obvious that its uses are not limited to the field of pulsoximetry and can instead be used in other measuring methods. This more particularly applies if a measuring method can be performed by irradiating electromagnetic waves into the human tissue. These include optical measuring methods, such as e.g. plethysmography.

Pulsoximetry is a non-invasive procedure for monitoring the state of a patient, particularly in the operating theatre or in the intensive care unit. Normally use is made of a sensor or transducer, particularly a finger sensor, into which are integrated light sources such as light emitting diodes (LEDs). It is possible to use two or more such LEDs with different wavelengths (e.g. in the red and infrared ranges). The light emitted by these light sources is introduced into the tissue of the patient to be monitored and photoreceivers, such as e.g. photodiodes or phototransistors, measure the intensity of the light transmitted through the tissue or reflected by it. During the transmission measurement, i. e. the measurement of the transmitted light, the transmitting and receiving diodes are placed on different sides of the human tissue, whereas they are on the same side of said tissue in the case of the reflection measurement.

The intensity measured on the reception side can, if a measurement takes place at at least two wavelengths, be used for calculating the oxygen saturation in the arterial blood of a patient. A good summary of the fundamental theory making use of Lambert-Beers absorption law is provided in EP-A-262 779. The sensor connected to the pulsoximeter via a detachable transducer cable normally contains at least two LEDs, which emit light e.g. having a wavelength of 650 nm—red and 1000 nm—infrared. By changing the exciting current in the transmitting diodes, it is possible to vary the intensity of the light emitted. The photocurrent received by the photoreceiver is measured by the pulsoximeter and used for calculating the oxygen saturation of the arterial blood.

It is obvious that pulsoximetric measurements are preferably performed on body parts to which a sensor can be easily applied or fitted and through which there is at the same time a good blood flow. For example, there are numerous forms of so-called ear sensors, i.e. sensors which are clipped to human earlobes through which there is a good blood flow.

However, the preferred application location in most practical cases is the human finger (the back of the foot in the case of newborn babies). Therefore numerous attempts have been made in the past to develop an optimum finger sensor for pulsoximetry. Therefore a large amount of patent literature exists in connection with this problem.

An earlier finger sensor type is e.g. described in U.S. Pat. No. 4,685,464. The quality of the signal supplied by the clothes peg-like sensor disclosed therein would probably be satisfactory, but it is stressful for the patient as a result of its size and weight and is also expensive as regards its mechanically complicated manufacture. Thus, nowadays such sensors are no longer used.

Thus, in practice finger sensors with a simpler construction are used. Such a sensor is e.g. described in German patent 3 703 458, where the sensor is made from an elastic material with a type of "geometrical reserve", making it possible to apply to the sensor to fingers of different thicknesses. The transmitting and receiving diodes are positioned on opposite sides of the sensor casing, so that said sensor is suitable for a transmission measurement. Similar sensors are disclosed by U.S. Pat. No. 5,035,243 and EP-A-572 684.

However, all these sensors still have the disadvantage that, due to their weight and in particular the mechanical compression of the finger tissue, they cannot be worn for an unlimited period. In many cases after even a few hours application the patient experiences discomfort. Other important disadvantages of such sensors that perspiration can collect under the sensor surface and impairs both the blood flow and the precision of the measured result, whilst due to the inner surfaces such sensors cannot be completely disinfected. Finally, a long application period with such sensors can even lead to tissue necrosis, even if the risk is relatively small.

Apart from the aforementioned pulsoximetry sensor variants, there are also disposable sensors, which can be stuck round the finger in the manner of a plaster. Such a sensor is described in EP-A-481 612. The sensor disclosed therein is admittedly lighter and is also suitable for a longer period of use, but still suffers from other disadvantages. From the measurement standpoint it is sensitive to surrounding light interference, because the measuring area is very open. In the case of imprecise application to the finger, this effect is exacerbated. The measurement of venous pulsations can also occur, whereas in actual fact only arterial pulsations are of interest. However, the main disadvantage is that, at least with respect to its adhesive part, it is not reusable. Other disadvantages of the closed, reusable sensor also appear in the disposable sensor, e.g. a deterioration of the measurement results due to the perspiration of the patient or allergic reactions (e.g. plaster allergy).

Therefore the problem of the present invention is to provide a novel pulsoximetry sensor, which is both reusable and suitable for long term use. A further aim of the invention is to provide a sensor with good measuring characteristics.

The usability of the sensor is not to be restricted to pulsoximetry (although this is certainly the main field of use), but also to other optical measuring methods on the human finger, such as e.g. plethysmography, or general measuring methods, in which electromagnetic waves are irradiated into the human finger tissue and the transmitted or reflected waves are measured.

BRIEF DESCRIPTION OF THE INVENTION

The invention relates to a sensor for performing medical measurements, particularly pulsoximetric measurements, on the human finger or toe, in which the electromagnetic waves are irradiated into the finger/toe and the characteristics of the radiation transmitted or reflected by the finger/toe are measured and having the following features:

a first casing part with a surface, which is partly concave and preferably cylindrical concave for adapting to the surface of a fingernail.

In the first casing part is embedded at least one electromagnetic transmitting and/or receiving element in such a way that the electromagnetic radiation can enter or exit said surface and an adhesive element transparent to the electromagnetic radiation and which, for fixing the sensor to the fingernail of the patient, is located on or can be applied to said surface of the first casing part.

The fundamental idea of the sensor according to the invention is that said sensor is to be fixed by means of an adhesive or sticking element directly to a fingernail of the patient, said fingernail being in principle randomly selectable. This fixing mode has the advantage that although an adhesive process can be used, little or no adhesive comes into contact with the skin, i.e. the risk of allergic reactions are reduced or completely eliminated. In addition, the fingernail allows a much more reliable fixing than a normal plaster, which is in contact with the skin.

As no allergic reactions have to be feared and as there is no necrosis risk, because the sensor according to the invention does not compress tissue, it is suitable in optimum manner for long term application. "Long term application" in the present case means any application or use lasting several hours, e.g. 2 hours (in certain known sensors, which envelop the finger tissue and can constrict the same, it is recommended that the application point, i.e. the patient's finger be changed every two hours).

The sensor according to the invention is also reusable, because, unlike with plaster-like sensors, it can be easily cleaned and disinfected. As it has few or no inner surfaces, sterilization is very reliable. It is also relatively open and consequently does not give rise to perspiration reactions on the human skin. Mention must finally be made of the limited overall size and the comparatively low price of the sensor according to the invention.

The sensor according to the invention has a first casing part with a surface, which roughly simulates the fingernail contour. Therefore the casing part can be relatively firm or rigid and this construction is also preferred. The adaptation is brought about by an at least partly concave shaping of said surface. The most suitable has proved to be a cylindrical concave shaping.

The fixing of the first casing part to the fingernail preferably takes place by means of an adhesive element transparent to electromagnetic radiation. In the case of an optical sensor, e.g. a pulsoximetric sensor, the adhesive element must consequently be at least partly optically transparent. The adhesive element is preferably constituted by an adhesive gel covered by a protective foil, roughly in the manner of adhesive tapes and whose protective foil can be removed, so that the adhesive surfaces becomes accessible. Another possibility consists of the use of a tissue-compatible adhesive which hardens and which, prior to the application of the sensor, is applied by the user to the concave surface of the first casing part of the sensor or to the patient's fingernail. Such adhesives can be dissolved again after use by suitable, medically harmless solvents and are already used in other applications, e.g. for EEG electrodes. However, it is also conceivable to use other adhesive elements, e.g. adhesive compounds or the like. Particular preference is given to an adhesive element contained in a cap which can be sucked by vacuum onto the finger or toe nail. It is merely necessary for it to be mounted, the vacuum lead being e.g. integrated into the sensor cable. All these embodiments are covered by the term "adhesive element".

A further feature of the sensor according to the invention is that at least one electromagnetic transmitting and/or receiving element is so embedded in the first casing part that the electromagnetic radiation can enter or exit said surface. In the case of a pulsoximeter or a comparable optical measuring device this can be in the form of light sources or receivers, preferably light emitting diodes (LEDs) and photoreceivers such as phototransistors or photodiodes.

Here several case distinctions can be made. In a preferred embodiment in the indicated surface of the first casing part and on different sides of its concave rounding are so embedded both an electromagnetic transmitter and an electromagnetic receiver that the axes of symmetry of the irradiation and reception of electromagnetic waves intersect within the finger tissue. In this case a so-called reflection sensor is obtained, i.e. the electromagnetic radiation is emitted by the tissue and the receiver records the intensity of the waves reflected by the tissue. If the electromagnetic radiation is in or close to the range of visible light, it is also recommended in this case to place an optical barrier, e.g. a black rubber tube between the optical transmitting element and optical receiving element. This optical barrier prevents radiation passing directly from the transmitter to the receiver and consequently improves the quality of the measured result. In another preferred embodiment the sensor according to the invention is designed as a so-called transmission sensor, i.e. the receiver does not measure the intensity of the radiation reflected by the tissue, but the intensity of the radiation passing through it. It is advantageous in this case to provide a second casing part, which at least partly surrounds the part of the finger/toe facing the finger/toe nail of the patient. It is then preferable for either the electromagnetic transmitter or the electromagnetic receiver to be embedded in the second casing part and the corresponding element in the first casing part. In other words, either the transmitter can be in the first casing part and the receiver in the second casing part, or said arrangement can be reversed. However, it is pointed out that the use of a second casing part, which increases wearing comfort and the reliable fastening to the finger, is recommended not only in the case of a transmission sensor, but also a reflection sensor.

The invention also proposes different preferred embodiments for the second casing part. In a first embodiment the casing part is shaped onto the first casing part and has elastic properties, i.e. it can be fixed to a certain degree on the fingertip and the elasticity provided ensures that there is little or no compression of the finger tissue and that the sensor can be placed on fingers of different thickness.

In an alternative embodiment the second casing part is pivotably articulated to the first casing part and the engagement on the finger is preferably achieved by spring action.

If the electromagnetic transmitting and receiving elements operate in the field of optical radiation, preferably in or close to the visible light range, it is also advantageous if the casing part or parts are at least partly made from transparent material. The casing parts can be made completely from transparent plastic, or it is possible to provide optically transparent "windows" in a casing part otherwise only slightly or not transparent for optical radiation.

In another advantageous embodiment there is a reflecting metallic or metallized foil, which extends at least over the back of the electromagnetic transmitting and/or receiving element. It firstly increases the radiation intensity in that it reflects back the light reradiated by the tissue and secondly it ensures that extraneous light cannot pass directly or through the tissue to the receiver. This foil, if it is connected to a cable screen, can also have an electrical screening effect.

The invention also relates to a method for performing medical measurements on the human finger, preferably optical measurements such as pulsoximetry, the method being characterized by the adhesion of a sensor provided with a concavely curved surface to a fingernail of a patient.

The most favourable measurement location is the thumb nail, because here there is generally a very good blood circulation and the thumb nail offers a large and relatively flat surface. However, any other fingernail can also be used. Finally, the invention also extends to the application of the sensor to a human toenail.

Apart from the aforementioned advantages, it is pointed out that the sensor according to the invention permits very good measurement results, because the corneum offers an optically much more transparent window to the tissue than the skin. Thus, direct optical access is provided to the well perfused tissue. Movement artefacts by sensor shifts are also largely avoided.

BRIEF DESCRIPTION OF THE DRAWINGS

The invention is described in greater detail hereinafter relative to a preferred embodiment and with reference to the attached drawings, wherein show.

DETAILED DESCRIPTION OF PREFERRED EMBODIMENTS

With the aid of the drawings two specific embodiments of pulsoximetry sensors will now be described, but it is obvious that the invention is not restricted to the pulsoximetry field.

Figure 1:
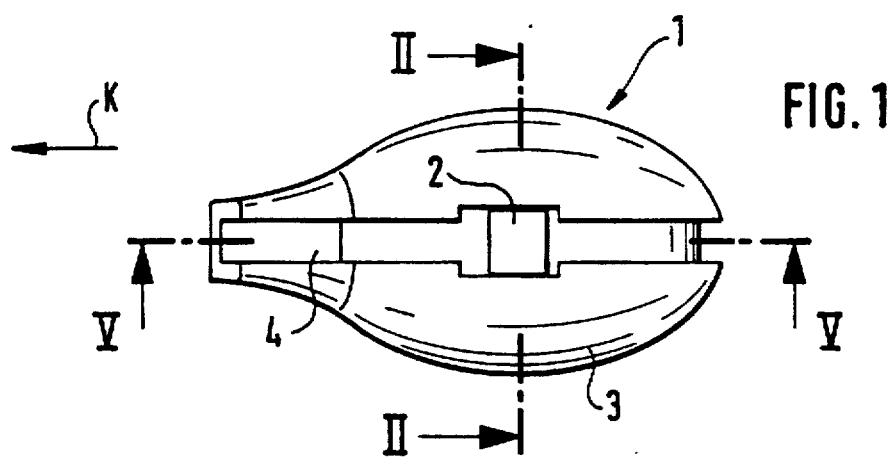
FIG. 1 A plan view of a transmission type sensor according to the invention.

The plan view of FIG. 1 shows a transmission sensor 1, in which is embedded a double light emitting diode or LED 2. This LED operates in the red and infrared ranges, as is conventionally the case in pulsoximetry. Only the first casing part 3 of the sensor 1 is visible in FIG. 1. The sensor is connected to a monitor by means of a not shown cable running in the direction of the arrow K. The cable is electrically connected to the light emitting diodes 2 and is inserted in a slot 4 of the sensor 1.

Figure 2:
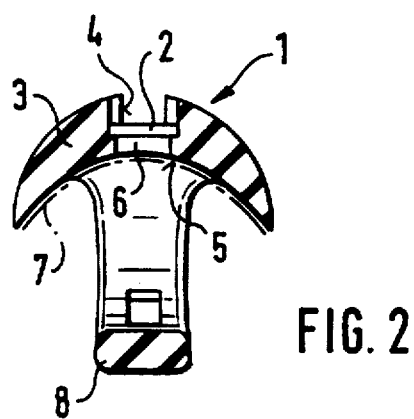
FIG. 2 A section through the sensor of FIG. 1 along reference line II—II.
Figure 4:
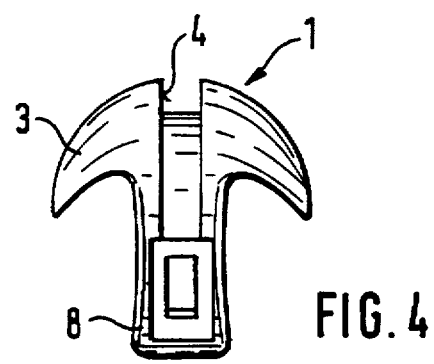
FIG. 4 A front view of this sensor.
Figure 3:
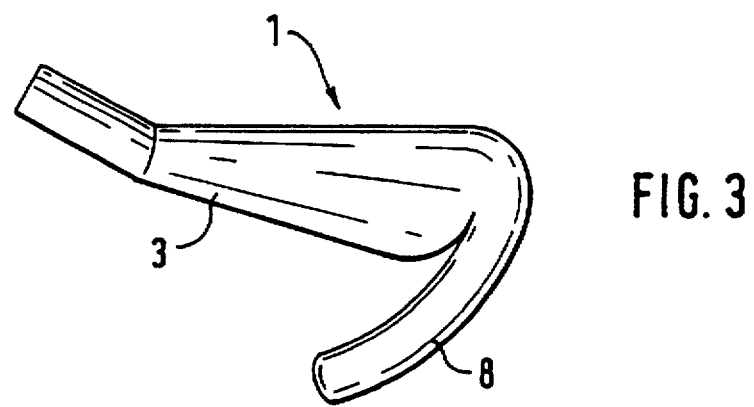
FIG. 3 A side view of the transmission sensor.
Figure 5:
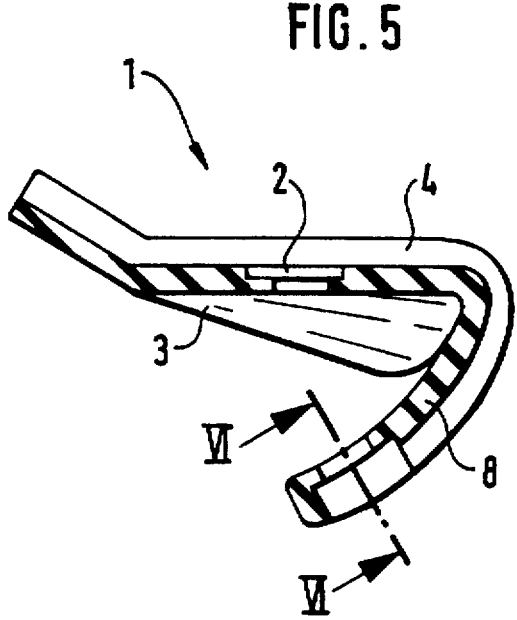
FIG. 5 A section along reference line V—V of FIG. 1.

In the cross-section of FIG. 2 it is once again possible to see a double LED 2, which is located on the bottom of the slot 4 of the first casing part 3. During application, the sensor is placed with a cylindrical concave surface 5 of the first casing part 3 on a finger or toe nail of a patient and is fixed there with an adhesive pad or a tissue-compatible adhesive. In order that the light from the double LED 2 can pass through the fingernail into the finger tissue, a recess 6 must be provided. Alternatively, at the location of reference numeral 6 can also be inserted transparent sensor material, such as e.g. transparent plastic.

Figure 6:
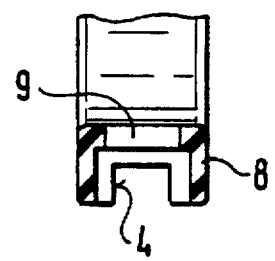
FIG. 6 A section along reference line VI—VI of FIG. 5.

The reference numeral 7 indicates an adhesive element or coating. A second casing part 8 with elastic properties passes round the finger or toe and thus ensures the mechanical fixing. Moreover, in the second casing part 8 is installed a photoreceiver (phototransistor, photodiode), which measures the intensity of the light radiated through the human tissue. This receiver is designated 9 in FIG. 6 and is also electrically connected to the cable and therefore the monitor.

Figure 7:
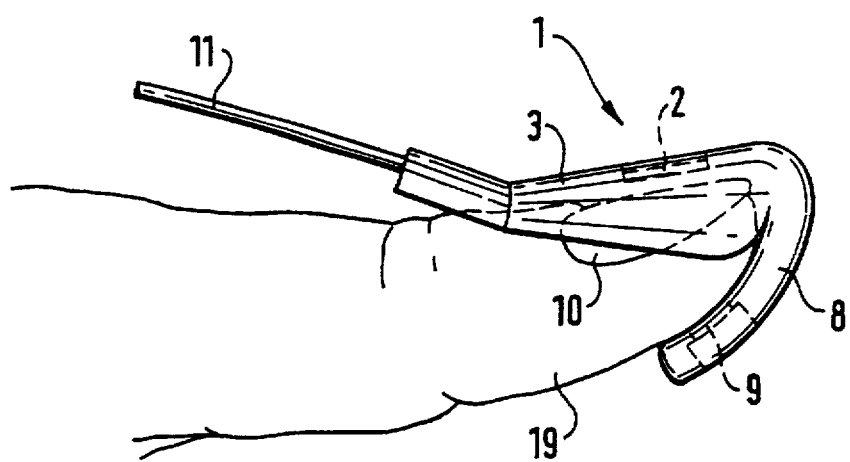
FIG. 7 An overall view of the applied sensor.

FIG. 7 diagrammatically shows the sensor 1 during the application to a human thumb 9. The adhesive element (adhesive pad or coating) is located between the thumb nail 10 and the sensor. The transmitting LEDs are drawn in diagrammatically and covered by the reference numeral 2, whereas the photoreceiver carries the reference numeral 9. It is also possible to see the cable 11 connecting the sensor to the monitor. The cable can also be tension-relieved by means of an armband, which is not shown in FIG. 7, but which will be discussed hereinafter using the example of a reflection sensor.

Figure 8:
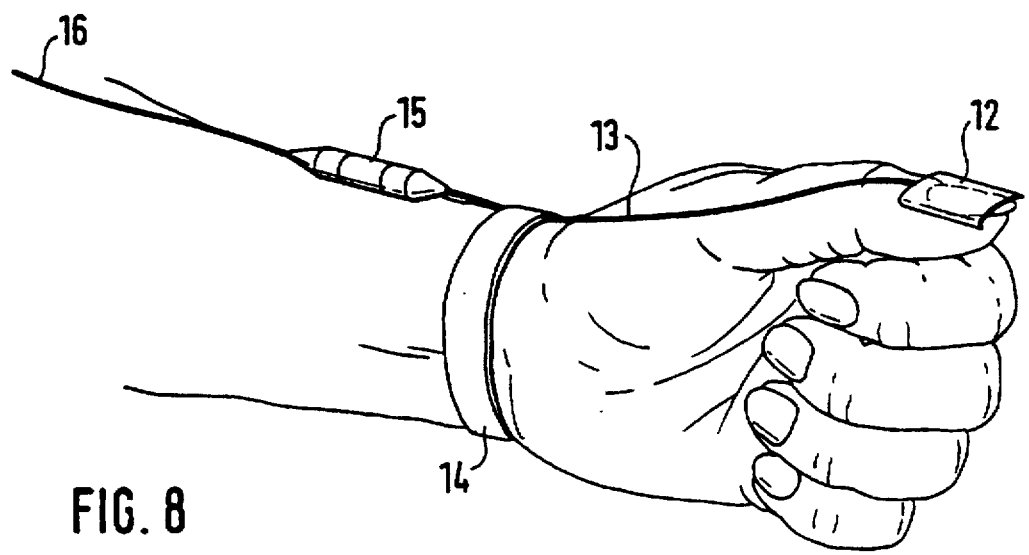
FIG. 8 The application of another embodiment, namely a reflection sensor.

FIG. 8 shows a reflection sensor 12, which is also stuck to the thumb nail of a patient. To the sensor is fixed a thin, light and flexible cable 13, which leaves the sensor in the direction of the forearm and is tension-relieved by an armband 14. A plug connection 15 is provided directly on or at the armband 14 and constitutes by means of a further, more robust cable 16 the connection to the measuring unit. Alternatively, the plug connection could be directly integrated onto the top of the sensor casing, so that cable 13 would be superfluous. The sensor casing is sealed, so that the sensor is not damaged by solvents used for removing the adhesive or cleaning and disinfecting agents.

Figure 9:
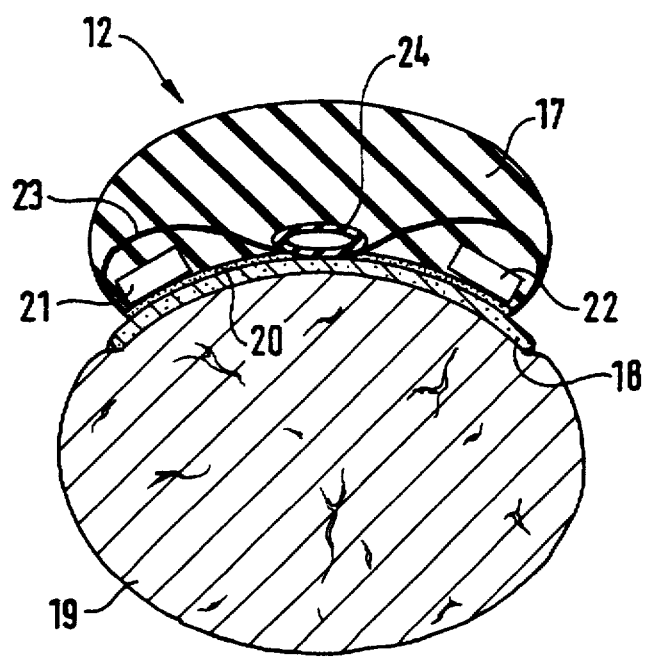
FIG. 9 A cross-section through the finger and the reflection sensor of FIG. 8.

In the cross-section through the reflection sensor of FIG. 9, it is possible to see that a first casing part 17 of the sensor 12 engages on the thumb nail 18 of a human thumb 19. The sensor is fixed to the thumbnail by means of an adhesive element and an adhesive coating 20. In the first casing part 17 is integrated a double transmitting LED 21, which irradiates into the tissue of the thumb 19 with red and infrared wavelengths. The reflected radiation is recorded by a photoreceiver 22.

A metal foil 23 screens the photoelements against surrounding light influences and brings about a focusing of the optical radiation. This is particularly necessary in the case of the receiving element 22, because the radiation passing through it is reflected by the metal foil 23 and can therefore be displayed. A thin, black rubber tube 24, which is compressed during application, serves as an optical barrier between the transmitting element 21 and the receiving element 22.

We claim:

1. A sensor for performing pulsoximetric measurements on the finger or toe of a patient, wherein electromagnetic waves are irradiated into the finger/toe and characteristics of radiation transmitted or reflected by the finger/toe are measured, said sensor comprising:

a first casing part that is substantially rigid and includes a contact surface which is at least partly concave for adapting to a surface of a fingernail or toenail;

at least one electromagnetic radiation transmitting and/or receiving element embedded in the first casing part so that electromagnetic radiation can enter or exit said surface of the first casing part; and, an adhesive element in contact with said contact surface and transparent to the electromagnetic radiation, for fixing said contact surface to the fingernail or toenail, wherein said contact surface is fixed to said fingernail or toenail solely by use of said adhesive element.

2. A sensor according to claim 1, wherein an electromagnetic transmitter and an electromagnetic receiver are so embedded in said surface of the first casing part that axes of symmetry of emission and reception of electromagnetic waves intersect within finger tissue or toe tissue.

3. A sensor according to claim 1, further comprising:
a second casing part coupled to said first casing part and formed to at least partly surround a part of a finger/toe that is opposite the fingernail or toenail of the patient.

4. A sensor according to claim 3, wherein either an electromagnetic transmitter or an electromagnetic receiver is embedded in the second casing part and a cooperating electromagnetic transmitter or an electromagnetic receiver, as the case may be, is located in the first casing part.

5. A sensor according to claim 3, wherein the second casing part has elastic properties and is shaped as part of the first casing part.

6. A sensor according to claim 3, wherein the second casing part is pivotally articulated to the first casing part.

7. A sensor according to claim 3, wherein said second casing part is at least partly flexible.

8. A sensor according to claim 1, wherein the electromagnetic transmitting and receiving elements operate in a range of optical radiation.

9. A sensor according to claim 8, wherein said first casing part is at least partly made from transparent material.

10. A sensor according to claim 8, further comprising:
a reflecting metallic or metallized foil extending at least over a back of the electromagnetic transmitting and/or receiving element.

11. A sensor according to claim 8, further comprising:
an optical barrier positioned between the optical transmitting element and the optical receiving element.

12. A sensor according to claim 1, wherein the adhesive element is an adhesive gel covered by a protective foil.

13. A sensor according to claim 1, wherein the adhesive element is a tissue-compatible adhesive.

14. A sensor according to claim 1, wherein the adhesive element is contained in a cap and can be sucked by vacuum therefrom onto the finger or toenail.

15. A method for performing medical optical measurements on the finger or toe of a patient comprising the steps of:

providing a substantially rigid electromagnetic radiation sensor with a concave surface;

applying an adhesive element that is transparent to electromagnetic radiation to said concave surface;

adhering said concave surface of said sensor to a fingernail or toenail of the patient solely by use of said adhesive element;

irradiating said fingernail or toenail, as the case may be, with electromagnetic radiation; and, sensing said electromagnetic radiation that exits said finger or toe with said sensor.

* * * * *